United States Patent [19]
Beals et al.

[11] Patent Number: 5,704,239
[45] Date of Patent: Jan. 6, 1998

[54] METHOD FOR CERAMIC PEENING OF ORTHOPAEDIC TITANIUM ALLOY IMPLANTS

[75] Inventors: Neil B. Beals, Memphis; Willard L. Sauer, Collierville, both of Tenn.

[73] Assignee: Smith & Nephew, Inc., Memphis, Tenn.

[21] Appl. No.: 583,924

[22] Filed: Jan. 11, 1996

[51] Int. Cl.$^6$ .................................................. B24C 1/10
[52] U.S. Cl. .................................. 72/53; 29/90.7; 451/38
[58] Field of Search ........................ 72/53; 29/90.7; 451/38, 39

[56] References Cited

U.S. PATENT DOCUMENTS 5,057,108  10/1991  Shetty et al. .............................. 606/53
5,251,468  10/1993  Lin et al. .................................. 72/53

OTHER PUBLICATIONS

"Shot Peening" by Robert B. Heaton, Metal Finishing, Jul., 1989.

Primary Examiner—David Jones
Attorney, Agent, or Firm—Pravel, Hewitt, Kimball & Krieger

[57] ABSTRACT

A method of preparing fretting wear resistant titaniumbase alloy orthopaedic implants includes the steps of shot peening the surface of the implant with spherical ceramic beads of a selected size and density, and with selected intensity such that the fretting wear resistance of the implant is increased and wherein the implant surface is uniformly peened to create a compressively-stressed region within the surface of approximately 100–300 microns depth.

29 Claims, 4 Drawing Sheets

METHOD FOR CERAMIC PEENING OF ORTHOPAEDIC TITANIUM ALLOY IMPLANTS

SPECIFICATION

BACKGROUND OF THE INVENTION

1. Field of the Invention

The present invention relates to surgical prosthetic devices and more particularly to orthopaedic surgical implants. Even more particularly, the present invention relates to a method of ceramic shot peening of titanium-base alloy orthopaedic surgical implants that improves such implants' resistance to fretting wear.

2. General Background

"Fretting wear" can be defined as the surface damage phenomenon that occurs on two adjacent contacting surfaces which experience oscillatory relative motion of small amplitudes (fretting). Fretting may also lead to fretting corrosion and fretting fatigue. Fretting corrosion relates to chemical reactions which take place at the fretting interface as a result of fretting. Fretting fatigue is related to fretting-initiated fatigue cracks which may result in component fatigue failure, as well as surface and subsurface stress concentrations.

Fretting wear is the loss of material (wear debris) that is associated with fretting conditions. When microscopic particles of metal are fretted from the metallic implant surface, the "fresh" metallic surface left behind by the newly removed particles releases metal ions there from. This ion release continues until the "fresh" surface becomes fully oxidized.

The July, 1989 issue of "Metal Finishing" by Robert B. Heaton described shot peening as a cold working process in which the surface of a metal part is bombarded with spherical particles (or shot) formed from cast iron, cast steel, stainless steel, ceramic or glass. The Heaton article states that peening is used to create a uniform compressive stress layer on or near the surface of metals that prolongs surface life under cyclical loading conditions by resisting fatigue failures. The Heaton article also discusses peening for application to leaf and coil springs, gear fillets, drive shafts, torsional bars, axles, oil well drilling equipment, turbine blade root, foil sections, and other metal components exposed to cyclical stresses.

A patent that describes a treatment process for a stainless steel orthopaedic implant device is U.S. Pat. No. 5,057,018 issued to H. Shetty, et al and entitled "Method of Surface Finishing Orthopedic Implant Devices". In the Shetty patent, a rough ground or machined stainless steel part is shot blasted with glass beads having a nominal size of between one-tenth and one-half that of the stainless steel shot. Electropolishing and passivation follow the shot blasting steps. A part thus treated includes a heavily cold-worked outer layer that is said to enhance the fatigue properties of the stainless steel orthopaedic implant device. The present invention is different from U.S. Pat. No. 5,057,018 in the following ways: i) it claims improvements for titanium alloy devices, not stainless steel devices; ii) the shot peening method described utilizes ceramic media, not stainless steel and glass media; and iii) improved surface properties which are claimed include only fretting wear resistance instead of fatigue and corrosion resistance.

SUMMARY OF THE INVENTION

The present invention provides a titanium-base alloy implant surface with improved resistance to fretting wear. A controlled ceramic shot peening process is used to induce a controlled surface roughness and uniform compressive stress on and into the surface of the titanium orthopaedic implant. These factors enhance the overall structural integrity of the implant and reduce the potential for metallic debris to be liberated from the implant as a result of metal-on-metal contact.

The present invention provides a method of preparing a controlled surface roughness of titanium orthopaedic implants by peening the surface of the implant with spherically shaped ceramic shot of a size, density, and selected peening intensity so that the fretting wear resistance of the implant is increased.

The present invention provides an improved method preparing fretting wear resistant titanium orthopaedic implants wherein the surface of the implant is shot peened with ceramic beads of a selected shot size, density, and selected peening intensity so that the fretting wear resistance of the implant is increased, and wherein the implant surface is peened such that a compressively-stressed region of approximately 100–300 microns in depth is produced.

In the method of the present invention, residual compressive stresses of at least 100 kpsi are produced within the surface of the titanium implant.

With the present invention, fretting wear debris generation is minimized.

In the preferred method of the present invention, the shot size is between 120 and 1200 microns diameter, the shot shape is spherical, the density (specific gravity) of the material from which the shot is composed is between 2.2 and 10.0 g/cm$^3$, the shot material composition includes any number of oxide ceramics such as $ZrO_2$, $Al_2O_3$, $SiO_2$, MgO, etc., the number fraction of non-spherical (including broken) shot is less than 5.0%, and the Almen intensity of the ceramic shot peening procedure is between 2.5 A and 18 A. In the preferred method of the present invention, the shot is filtered to remove any non-spherical or particulate shot material prior to peening operations, surface coverage is 100–200%, and the peening procedure is fully automated to ensure uniform coverage over the entire peened surface.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

The present invention provides a method for forming the surface of titanium alloy orthopaedic implants such as hip implants, knee implants, spinal implants, and the like. This material is used for such applications due to its high fatigue strength, low elastic modulus, and excellent biocompatibility and corrosion resistance.

The ceramic shot used to peen the titanium-alloy surface is preferably 120–1200 microns in diameter, the shot density (specific gravity) is preferably 2.2–10.0 g/cm$^3$, the shot composition is preferably any of a number of oxide ceramics or mixtures thereof. The number fraction of non-spherical shot is preferably less than 5.0%. The Almen intensity is preferably 2.5 A–18 A. Surface coverage is preferably 100–200%. The peening procedure is preferably automated to ensure uniform surface coverage.

Figure 1:
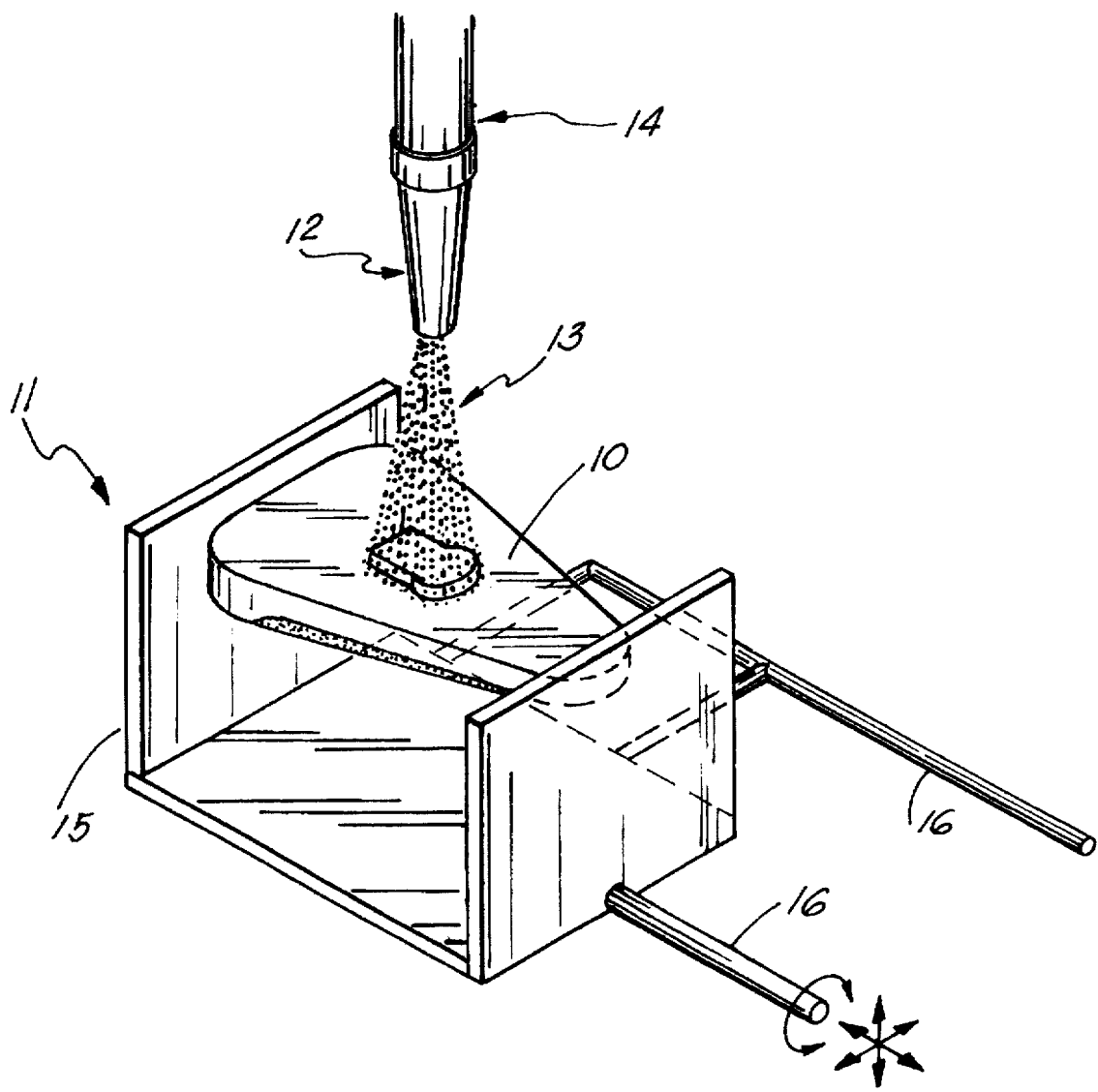
FIG. 1 is a schematic representation of the shot peening nozzle and specimen fixture associated with the automated bead blasting apparatus of the type used in accordance with the method of the present invention, wherein a modular titanium alloy component is being processed.

Referring now to FIG. 1, there can be seen a shot peening nozzle 12 and specimen fixture assembly 11 of the type used in conjunction with a shot peening apparatus (not shown) in carrying out the process and producing an orthopaedic implant workpiece 10 in accordance with the present invention. Nozzle 12 is used to carry and expel ceramic media 13 with high pressure air toward a target area of workpiece 10. The nozzle is connected to a hose 14, which is connected to a dry blast system with a cyclone media separator and dust blower (not shown) or similar features which are used to recirculate only undamaged spherical ceramic shot.

Assembly 11 includes a fixture 15 for supporting and manipulating workpiece 10 which in turn is connected to arms 16 which are compatible with an automated, programmed motion system (not shown) used to control the location, angle, and coverage of peening of workpiece 10.

The metal substrate of implant workpiece 10 in FIG. 1 is preferably wrought and annealed titanium-6 aluminum-4 vanadium (Ti-6Al-4V) alloy (R$_c$30–35), but the method of the present invention is applicable to any titanium-base alloy in any metallurgical condition. The surface finish of workpiece 10 is preferably polished or machined with a surface roughness (Ra)of 128 microinches or less. Following the ceramic peening surface treatment, the titanium-alloy surface is preferably not given any additional surface treatments which may physically alter the surface. The surface is, however, preferably cleaned and passivated in accordance with conventional methods. These steps are conducted to remove loosely attached debris, remove most surface contamination, and reinforce the passive surface oxide layer.

Figure 2:
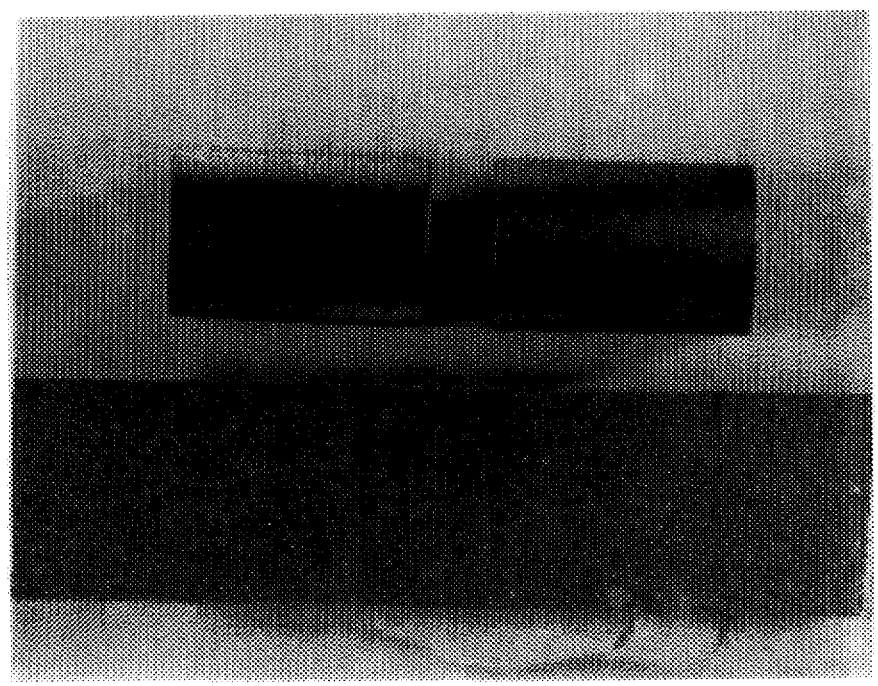
FIG. 2 is a photograph (1× magnification) of both curved and flat orthopaedic titanium alloy surfaces processed according to the ceramic shot peening method of the present invention.

In FIG. 2, there can be seen ceramic shot peened orthopaedic titanium alloy surfaces at 1× magnification. The alloy (Ti-6Al-4V) has been peened with spherical ceramic shot.

Figure 3:
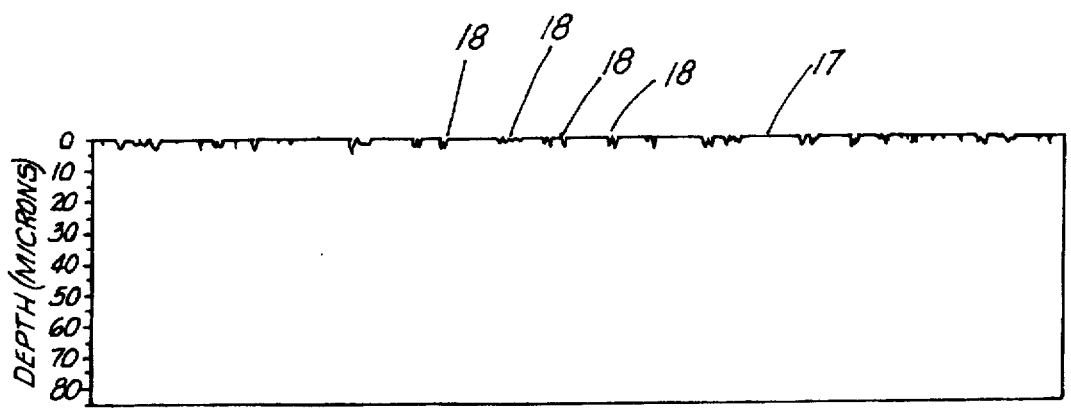
FIG. 3 is a schematic representation of a cross-section of a titanium implant surface showing initial microscopic defects at the surface.

In FIG. 3, a schematic of a machined titanium implant surface 17 is shown having microscopic surface defects 18.

Figure 4:
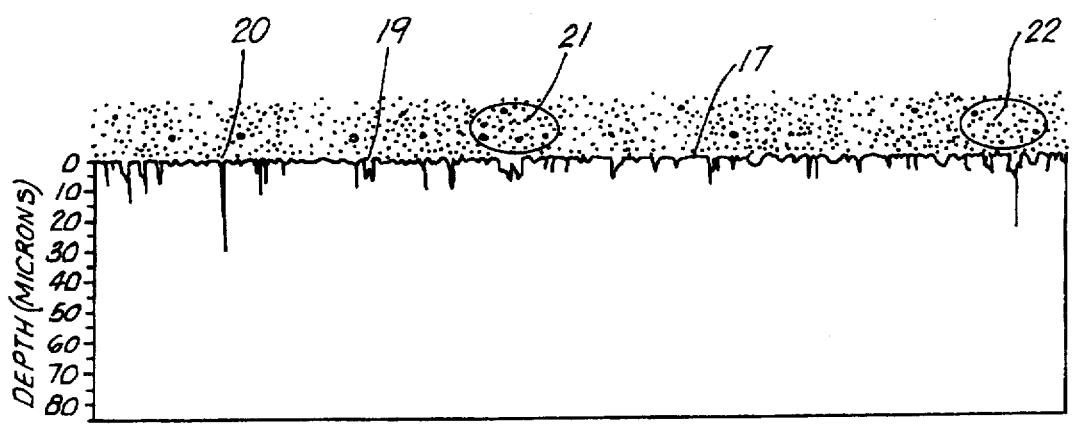
FIG. 4 is a schematic representation of the implant surface of FIG. 2 after some time "t" of metal-on-metal fretting.

In FIG. 4, the same surface 17 is shown after some time "t" where fretting wear has occurred, producing larger cracks and defects 19, 20 and escaping debris 21, 22.

In FIG. 4, a schematic of a machined and ceramic shot peened titanium implant surface 23 is shown having microscopic surface defects 24 and a compressively stressed sub-surface region 25.

Figure 5:
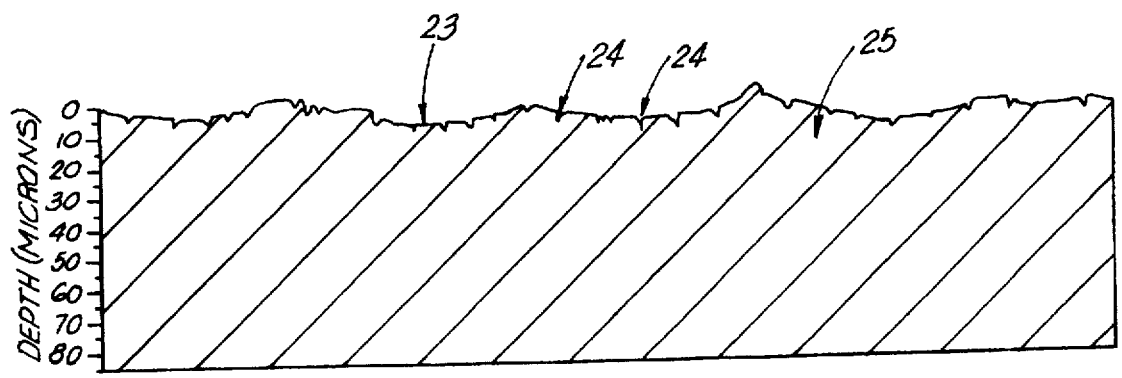
FIG. 5 is a schematic representation of the implant surface of FIG. 2, ceramic shot peened according to the method of the present invention. The shading represents the relative degree of compressive stresses within the surface.
Figure 6:
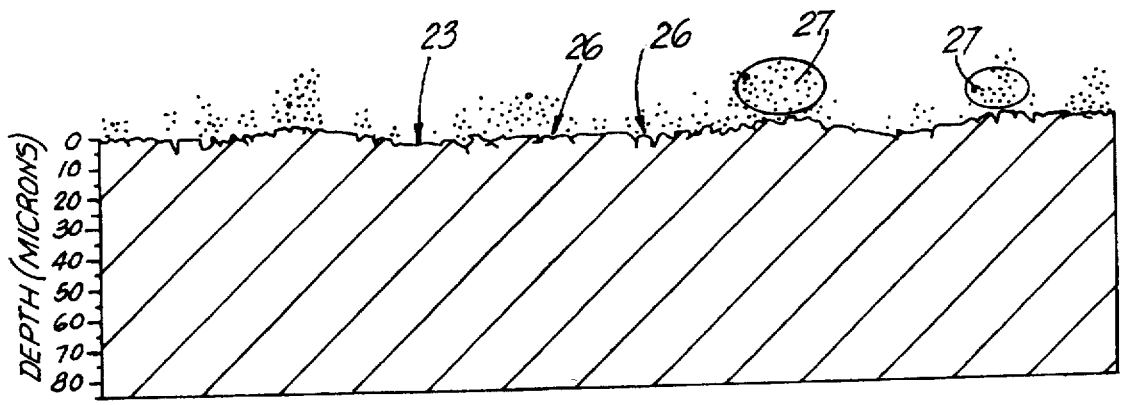
FIG. 6 is a schematic representation of the implant surface of FIG. 4 after some time "t" of metal-on-metal fretting.

In FIG. 5, the same surface 23 is shown after some time "t" where fretting wear has occurred producing less cracks and defects 26 and less escaping debris 27 compared to the non-peened surface in FIG. 3.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of preparing fretting wear resistant titanium alloy orthopaedic implants, comprising the steps of:

a) shot peening the surface of the titanium alloy implant with ceramic beads of a selected shot size, shape, and with selected intensity and coverage uniformity so that the fretting wear resistance of the implant is increased; and b) wherein the implant surface area is peened such that a compressively-stressed region of approximately one hundred to three hundred (100–300) microns in depth is achieved.

2. The method of claim 1 wherein the titanium implant is subjected to cyclical loading conditions during use by a patient.

3. The method of claim 1 wherein the titanium implant has a first surface that is subjected to oscillatory relative motion with a second surface.

4. The method of claim 1 wherein there are two adjacent contacting surfaces of the implant which experience oscillatory relative motion of small amplitude.

5. The method of claim 1 wherein in step "a" the surface is compressively-stressed by ceramic shot peening.

6. The method of claim 1 wherein the fretting wear debris generation is minimized.

7. The method of claim 1 further comprising the step of producing residual compressive stresses of at least one hundred (100) Kpsi within the surface area of the titanium implant.

8. The method of claim 1 wherein step "a" includes shot peening with shot of a sized between about one hundred twenty and twelve hundred (120–1200) microns diameter.

9. The method of claim 1 wherein step "a" includes shot peening with spherical shot.

10. The method of claim 1 wherein step "a" includes shot peening with ceramic shot of a material having a density (specific gravity) of between about 2.2 and 10.0 g/cm$^3$.

11. The method of claim 1 wherein step "a" includes shotpeening with shot material of oxide ceramic.

12. The method of claim 1 wherein step "a" includes shotpeening with Almen intensity between about 2.5 A and 18 A.

13. The method of claim 1 further comprising the step of filtering the shot to remove any non-spherical shot material prior to the shotpeening step "a".

14. A method of preparing a controlled surface roughness of titanium orthopaedic implants, comprising the steps of:

a) shot peening the surface of the implant with generally selected spherically shaped ceramic shot of a size, density, and selected Almen intensity so that the fretting wear resistance of the implant surface area is increased.

15. The method of claim 14 wherein the surface of the implant is titanium-base alloy.

16. The method of claim 14 further comprising the step of subjecting the titanium implant to cyclical loading conditions.

17. The method of claim 14 wherein the titanium implant has a first surface and a second surface and further comprising the step of subjecting the first surface to oscillatory relative motion with the second surface.

18. The method of claim 14 wherein there are two adjacent contacting surfaces of the implant and further comprising the step of subjecting the contacting surfaces oscillatory relative motion of small amplitude.

19. The method of claim 14 wherein the peening almen intensity is between 2.5 A and 18 A.

20. The method of claim 14 wherein a compressively-stressed region within the surface of approximately 100–300 microns in depth is created.

21. The method of claim 14 where, prior to peening, the shot is filtered to remove non-spherical shot such that the number fraction of such shot is less than 5.0%.

22. The method of claim 14 wherein an automated peening process is utilized to ensure a uniform, pre-selected peening coverage of 100–200%.

23. The method of claim 14 further comprising the step of producing residual compressive stresses of at least one hundred (100) Kpsi within the surface area of the titanium implant.

24. The method of claim 14 wherein step "a" includes shot peening with shot of a sized between about one hundred twenty and twelve hundred (120–1200) microns diameter.

25. The method of claim 14 wherein step "a" includes shot peening with spherical shot.

26. The method of claim 14 wherein step "a" includes shot peening with shot of a material having a density (specific gravity) of between about 2.2 and 10.0 g/cm$^3$.

27. The method of claim 14 wherein step "a" includes shotpeening with shot material of oxide ceramic.

28. The method of claim 14 wherein step "a" includes shotpeening with almen intensity between about 2.5 A and 18 A.

29. The method of claim 14 further comprising the step of filtering the shot to remove any non-spherical shot material prior to the shotpeening step "a".

\* \* \* \* \*